(12) United States Patent
Matsumura (10) Patent No.: US 9,851,810 B2
(45) Date of Patent: Dec. 26, 2017

(54) INFORMATION TERMINAL DEVICE AND BIOLOGICAL SAMPLE MEASUREMENT DEVICE

(75) Inventor: Keisuke Matsumura, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 81 days.

(21) Appl. No.: 13/984,172

(22) PCT Filed: Feb. 20, 2012

(86) PCT No.: PCT/JP2012/001123
§ 371 (c)(1),
(2), (4) Date: Aug. 7, 2013

(87) PCT Pub. No.: WO2012/117689
PCT Pub. Date: Sep. 7, 2012

(65) Prior Publication Data
US 2013/0328782 A1  Dec. 12, 2013

(30) Foreign Application Priority Data
Mar. 1, 2011  (JP) .................................. 2011-043484

(51) Int. Cl.
*G06F 3/02* (2006.01)
*G06F 3/023* (2006.01)
(Continued)

(52) U.S. Cl.
CPC ........ *G06F 3/0233* (2013.01); *A61B 5/14532* (2013.01); *A61B 5/7475* (2013.01); *G06F 1/1626* (2013.01); *G06F 3/0236* (2013.01)

(58) Field of Classification Search
CPC ........ G06F 3/018–3/027; G06F 1/1626; A61B 5/7475; A61B 5/14532
(Continued)

(56) References Cited

U.S. PATENT DOCUMENTS 6,232,970 B1 * 5/2001 Bodnar ................. G06F 3/0236
715/210
6,897,849 B2 * 5/2005 Kim ....................... G06F 3/0236
341/20
(Continued)

FOREIGN PATENT DOCUMENTS

JP 2004-354207 12/2004
JP 2006-293797 10/2006
(Continued)

OTHER PUBLICATIONS

International Search Report dated May 22, 2012 in International (PCT) Application No. PCT/JP2012/001123.
(Continued)

*Primary Examiner* — Roberto Flores
(74) *Attorney, Agent, or Firm* — Wenderoth, Lind & Ponack, L.L.P.

(57) ABSTRACT

In an information terminal device (100), a display component (2) displays, on the basis of commands from a controller (9), a plurality of character keys, an enter key (20) for entering input information including one or more characters inputted by selecting the plurality of character keys, and a selection marker indicating one of the plurality of character keys being selected. An input component (3) includes a select key (5) that causes the controller (9) to successively move the selection marker displayed on the display component (2) over the plurality of character keys so as to select one of the character keys, and a change key (8) that causes the controller (9) to change a display content of the display component (2). When the change key (8) has been operated in a state in which the input information is being displayed on the display component (2), the controller (9) moves the selection marker displayed on the display component (2) from the selected character key directly to the enter key (20).

4 Claims, 9 Drawing Sheets

(51) Int. Cl.
*G06F 1/16* (2006.01)
*A61B 5/00* (2006.01)
*A61B 5/145* (2006.01)

(58) Field of Classification Search
USPC .................................................. 345/156–183
See application file for complete search history.

(56) References Cited

U.S. PATENT DOCUMENTS

| | | | | |
|---|---|---|---|---|
| 8,037,495 | B2* | 10/2011 | Morita et al. .................... | 725/52 |
| 8,887,101 | B2* | 11/2014 | Huang ............................ | 715/856 |
| 2001/0019423 | A1* | 9/2001 | Hirai ....................... | G06K 15/02 |
| | | | | 358/1.15 |
| 2002/0163543 | A1* | 11/2002 | Oshikiri ........................ | 345/810 |
| 2002/0180689 | A1* | 12/2002 | Venolia ................. | G06F 3/0237 |
| | | | | 345/156 |
| 2003/0001816 | A1* | 1/2003 | Badarneh ....................... | 345/156 |
| 2004/0135823 | A1* | 7/2004 | Wingett et al. ............... | 345/856 |
| 2004/0239637 | A1* | 12/2004 | Williams et al. .............. | 345/172 |
| 2004/0261103 | A1* | 12/2004 | Ohno et al. ....................... | 725/38 |
| 2005/0068292 | A1* | 3/2005 | Duarte et al. .................. | 345/156 |
| 2007/0013665 | A1* | 1/2007 | Vetelainen et al. ........... | 345/169 |
| 2007/0015534 | A1* | 1/2007 | Shimizu ..................... | 455/550.1 |
| 2007/0279389 | A1* | 12/2007 | Hoch et al. .................... | 345/169 |
| 2007/0291006 | A1* | 12/2007 | Park ....................... | G06F 3/0238 |
| | | | | 345/169 |
| 2007/0294636 | A1* | 12/2007 | Sullivan ................ | G06F 3/0236 |
| | | | | 715/810 |
| 2008/0042983 | A1* | 2/2008 | Kim .................... | G06F 3/03547 |
| | | | | 345/173 |
| 2008/0072143 | A1* | 3/2008 | Assadollahi .......... | G06F 3/0236 |
| | | | | 715/261 |
| 2008/0074389 | A1* | 3/2008 | Beale ........................... | 345/161 |
| 2009/0058810 | A1* | 3/2009 | Kikuchi .............. | G06F 3/04892 |
| | | | | 345/168 |
| 2010/0171706 | A1* | 7/2010 | Tsuruzono ............ | G06F 3/0236 |
| | | | | 345/168 |
| 2011/0172498 | A1* | 7/2011 | Olsen et al. .................. | 600/300 |
| 2011/0224499 | A1* | 9/2011 | Banet ....................... | A61B 5/00 |
| | | | | 600/300 |

FOREIGN PATENT DOCUMENTS

| | | |
|---|---|---|
| JP | 2008-58148 | 3/2008 |
| JP | 2010-69193 | 4/2010 |

OTHER PUBLICATIONS

Ken'ichiro Yasuhara, Waga Ryu o Miyo "Pride of the Dragon Peace" Software Manual, Sony Computer Entertainment Inc., Oct. 28, 2004 (Oct. 28, 2004) (received date), p. 09 along with partial English translation of p. 9.

Dragon Quest Shonen Yangasu to Fushigi no Dungeon, Square Enix, Apr. 27, 2006 (Apr. 27, 2006) (received date), p. 10 along with partial English translation of p. 10.

* cited by examiner

INFORMATION TERMINAL DEVICE AND BIOLOGICAL SAMPLE MEASUREMENT DEVICE

TECHNICAL FIELD

The present invention relates to an information terminal device, and more particularly to a biological sample measurement device for measuring biological samples, such as the blood glucose level.

BACKGROUND ART

If we assume that a biological sample measurement device for measuring blood glucose levels is used in a hospital, for example, where there are many operators and many patients, the operators and the patients using the device need to be identified. Therefore, ID's must be assigned to the operators and patients, and inputted into the device.

For inputting information in the past, an information terminal device was provided with a display component and a plurality of character keys indicating characters or numbers arranged in an array beneath the display component (see Patent Literature 1 below, for example).

CITATION LIST

Patent Literature

Patent Literature 1: Japanese Laid-Open Patent Application 2006-293797

SUMMARY

Technical Problem

When a configuration for inputting characters, etc., in a terminal device was used in a biological sample measurement device as described above, the device ended up being bulky and less convenient to use. Specifically, in a case where a plurality of character keys indicating characters or numbers were arranged in an array beneath the display component as discussed above in order to input the ID's of patients and operators, the device ended up being correspondingly larger.

There have therefore been attempts at reducing the size by displaying character keys within the display component and selecting the character keys in the display component by using an input means provided near the display component. In this case, first a select key of the input component is operated to move the cursor successively over the characters in the display component. Then the character keys are successively selected in the display component, and as a result, an ID consisting of a plurality of numbers is inputted. Next, the select key of the input component is used to move the cursor further and select an enter key within the display component, and enter the inputted ID.

However, if the enter key and the character key last selected and inputted are displayed far apart in the display component, the cursor will have to move a greater distance, which means that it takes longer to reach the enter key. This made the biological sample measurement device less convenient to use.

In view of this, it is an object of the present invention to improve the efficiency of the input operation in an information terminal device.

Solution to Problem

The information terminal device disclosed herein comprises a main body case, a display component provided at a face of the main body case, an input component provided at the face of the main body case and provided near the display component, and a controller connected to the input component and the display component. The controller is configured to control a display of the display component. The display component is configured to display, on the basis of commands from the controller, a plurality of character keys, an enter key for entering input information including one or more characters inputted by selecting one or more of the plurality of character keys, and a selection marker indicating one of the plurality of character keys being selected. The input component includes a select key that causes the controller to successively move the selection marker displayed on the display component over the plurality of character keys so as to select one of the character keys, and a change key that causes the controller to change a display content of the display component. When the change key has been operated in a state in which the input information is being displayed on the display component, the controller moves the selection marker displayed on the display component from the selected character key directly to the enter key.

Advantageous Effects

With the above-mentioned information terminal device, the efficiency of the input operation can be improved.

DESCRIPTION OF EMBODIMENTS

An embodiment of the present invention will be described through reference to the drawings, using a portable biological sample measurement device for measuring blood glucose levels as an example.

1. Embodiment 1

1.1 Appearance of Blood Glucose Level Measurement Device 100

Figure 1:
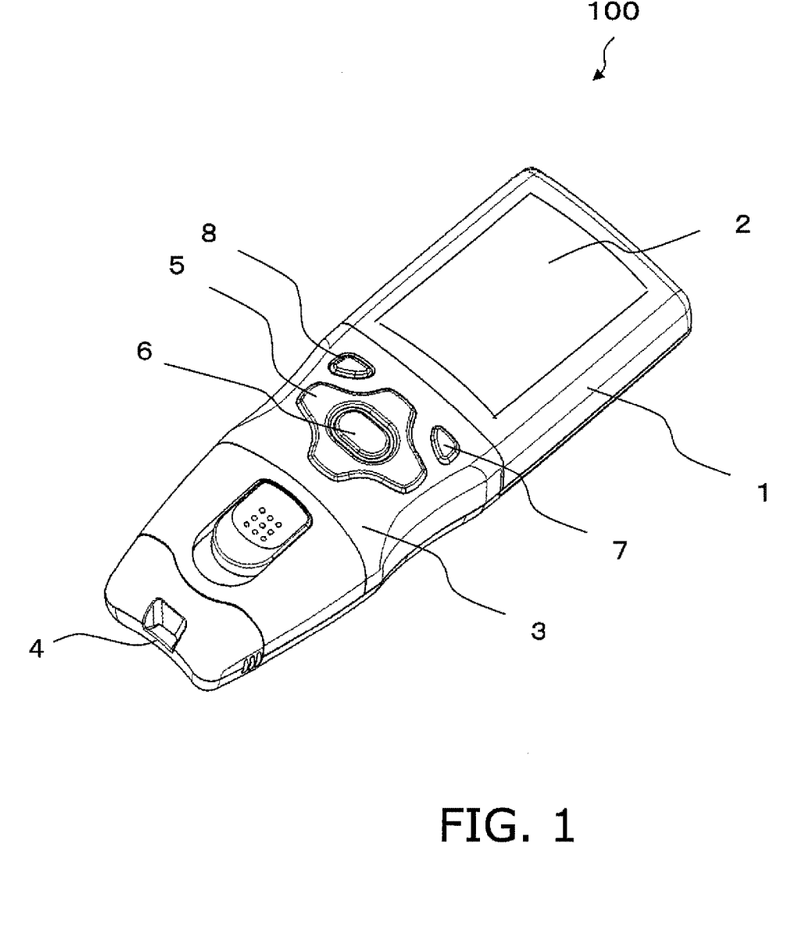
FIG. 1 is an oblique view of a portable biological sample measurement device in an embodiment of the present invention.

FIG. 1 illustrates a blood glucose level measurement device 100 (an example of an information terminal device or a biological sample measurement device) pertaining to this embodiment. The blood glucose level measurement device 100 comprises a substantially cuboid main body case 1, a display component 2 provided to the upper face of this main body case 1, an input component 3 provided beneath this display component 2, and an insertion opening 4 that is provided to the lower end of the main body case 1 and into which a blood glucose level sensor (not shown) is inserted.

The input component 3 has a cross key 5 that is used as a select key, a set key 6 (an example of a first push button) that is provided in the center of the cross key 5 and is operated by pressing, a power switch 7 that is provided near the cross key 5 and is operated by pressing, and a home key 8 (an example of a change key or a second push button) that is also provided near the cross key 5 and is operated by pressing. The cross key 5, as will be discussed below, is used to move a cursor (an example of a selection marker) within the display component 2. The set key 6 is used to set information that has been selected with the cursor. The power switch 7 functions as a switch for turning the power on and off. The home key 8 is used to change the display content displayed on the display component 2.

1.2 Control Blocks of Blood Glucose Level Measurement Device 100

Figure 2:
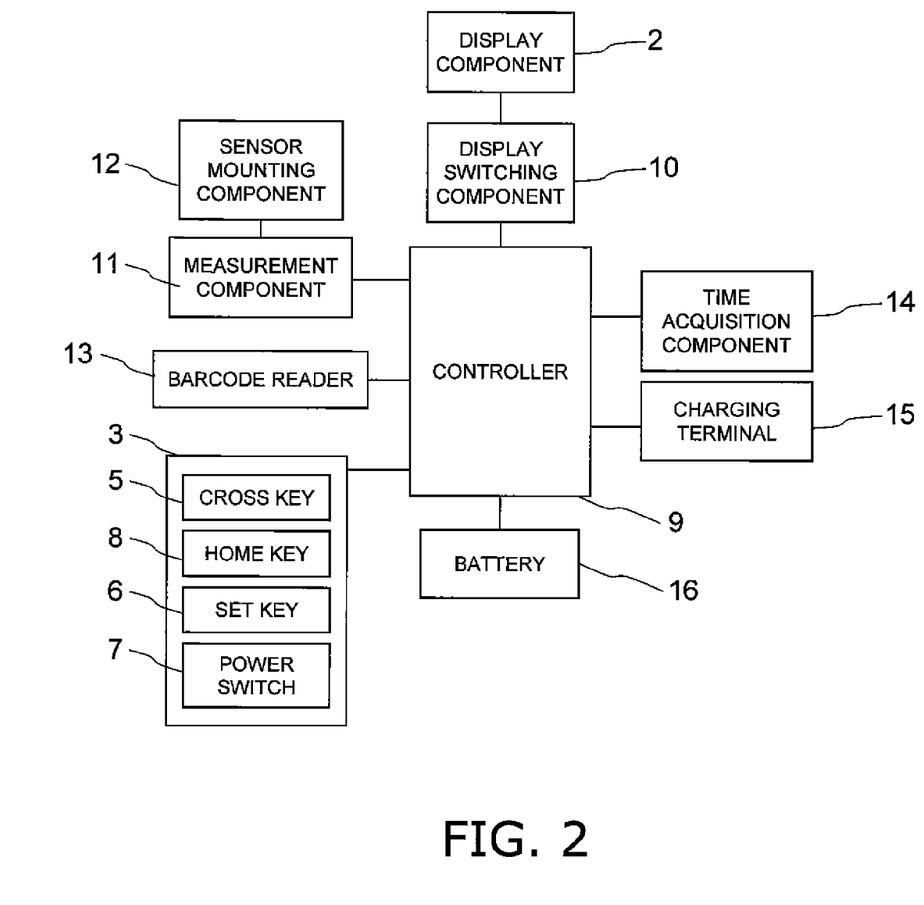
FIG. 2 is a control block diagram of the biological sample measurement device.

FIG. 2 is a control block diagram of the blood glucose level measurement device 100. The input component 3 is connected to a controller 9. The controller 9 (an example of a controller) is also connected to the display component 2 via a display switching component 10 (an example of a controller). This controller 9 is further connected to a sensor mounting component 12 via a measurement component 11. The sensor mounting component 12 is disposed within the main body case 1 to the rear of the insertion opening 4. The controller 9 is further connected to a barcode reader 13. This barcode reader 13 is provided to the end of the main body case 1 on the opposite side from the insertion opening 4. The controller 9 is also connected to a time acquisition component 14, a charging terminal 15, a battery 16, and so forth.

1.3 Operation of Blood Glucose Level Measurement Device 100

1.3.1 Measurement Processing

Figure 3A:
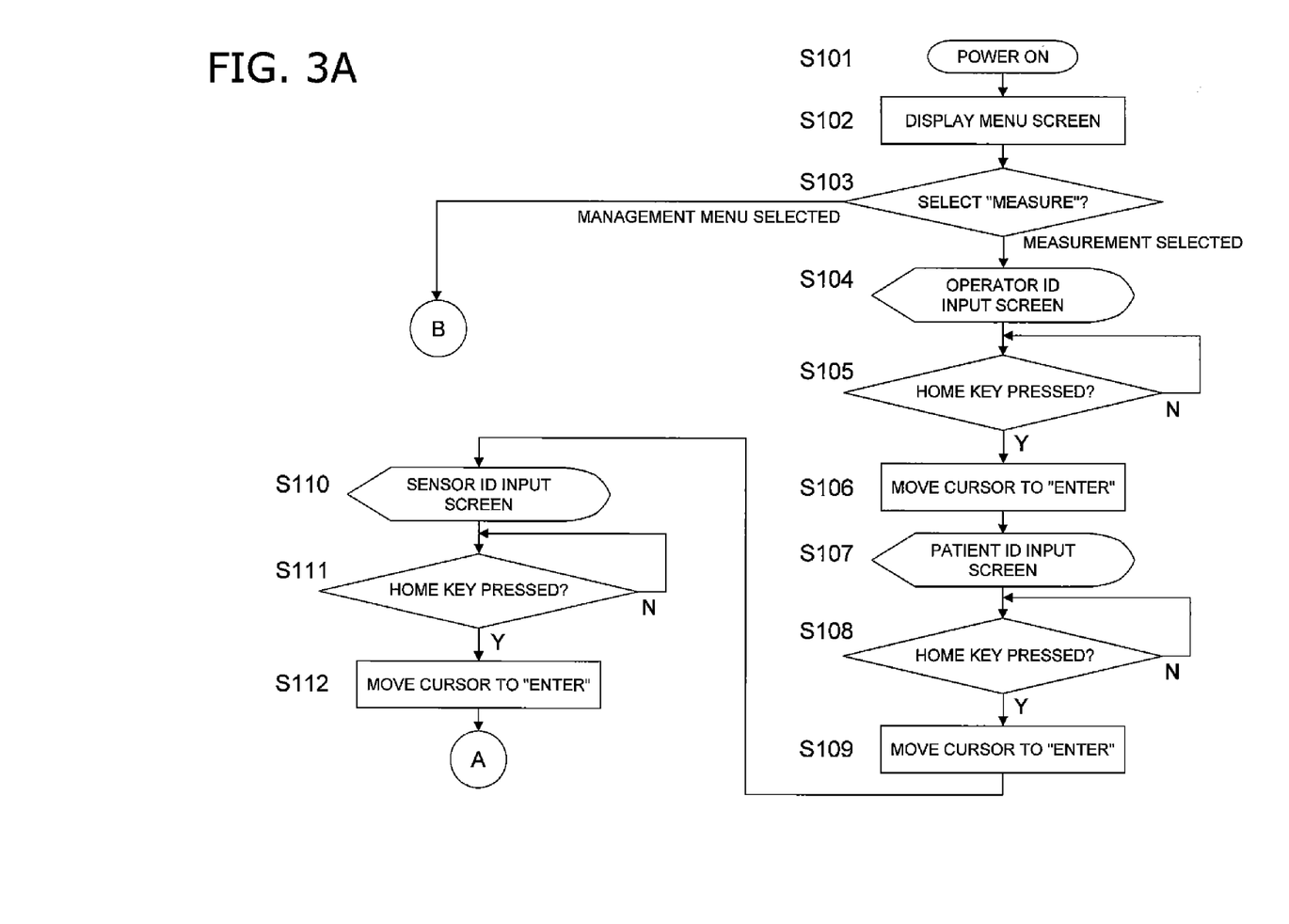
FIG. 3A is an operation flowchart of the biological sample measurement device.
Figure 3B:
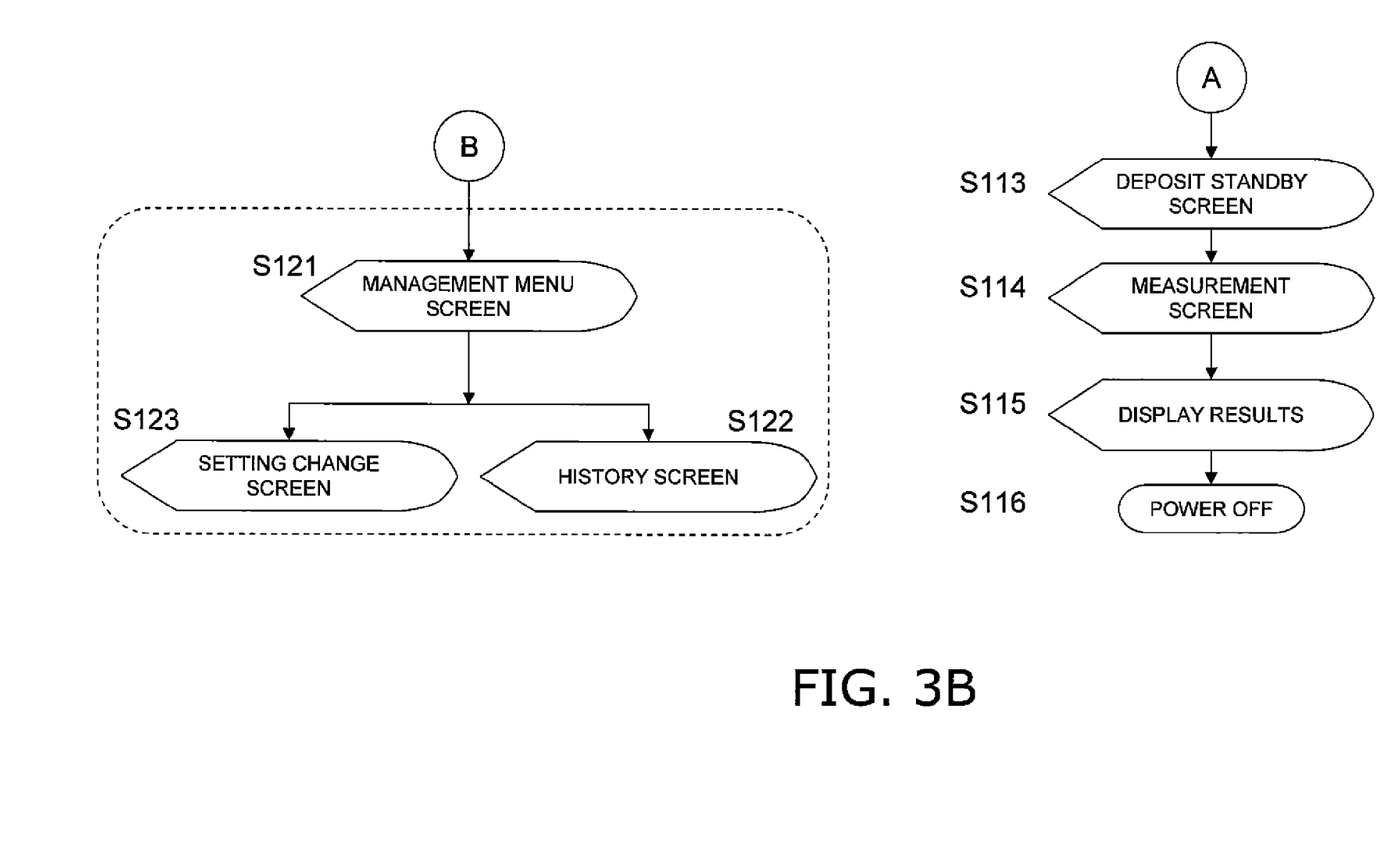
FIG. 3B is an operation flowchart of the biological sample measurement device.

FIGS. 3A and 3B are operation flowcharts of the display component 2 when a blood glucose level is to be measured. The operation of the display component 2 will now be described through reference to FIGS. 1 to 3.

Step S101: As shown in FIG. 3A, the power is turned on when the user presses the power switch 7 (or the power may be turned on in response to a blood glucose level sensor being mounted, etc.).

Figure 4A:
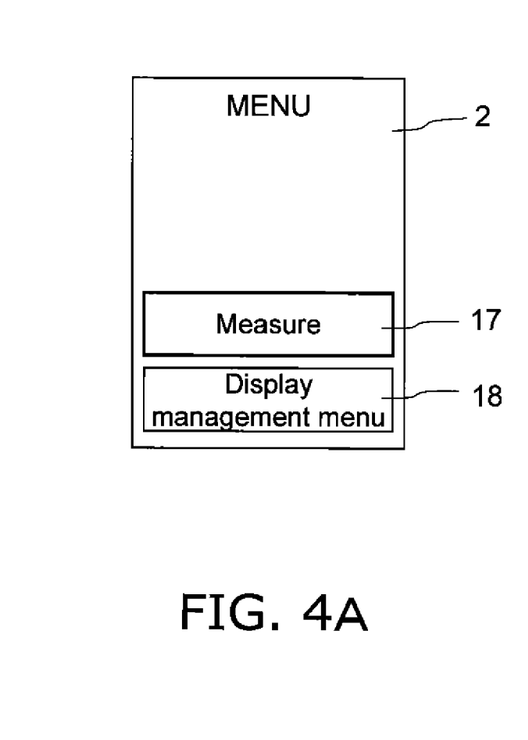
FIG. 4 shows an example of what is displayed on the display component of the biological sample measurement device.

Step S102: In response to the power being turned on, the controller 9 instructs the display switching component 10 to display the menu screen shown in FIG. 4A on the display component 2. As shown in FIG. 4A, a measurement menu area 17 and a management menu area 18 are displayed on the menu screen. When the menu screen is displayed, the measurement menu area 17 is highlighted, that is, it is in a selected state.

Step S103: When measurement is to be performed, the user presses the set key 6 to set the measurement menu that is highlighted on the display component 2. If no measurement is to be performed and the management menu is selected, the flow proceeds to step S111 (discussed below).

Step S104: When the set key 6 is pressed, the controller 9 instructs the display switching component 10 to display an input screen for the operator ID (an example of input information or identification information about the operator) on the display component 2, and the input of the operator ID is accepted. The input of the operator ID, which will be discussed below, is accomplished by moving the cursor to one of the character keys, selecting, and setting the character keys, and repeating this procedure.

Steps S105 and S106: Once the input of the last character key for the operator ID is complete, the home key 8 is pressed by the user. At this point the controller 9 instructs the display switching component 10 to move the cursor on the display component 2 directly to an enter key 20.

Step S107: When the set key 6 is pressed, input of the operator ID is entered. After verification of the operator ID, the controller 9 then instructs the display switching component 10 to display a patient ID input screen on the display component 2, and input of patient ID (an example of input information or identification information about the patient) is accepted. The input operation is the same as with the input of the operator ID.

Step S108 and S109: Once the input of the last character key for the patient ID is complete, the home key 8 is pressed by the user. At this point the controller 9 instructs the display switching component 10 to move the cursor on the display component 2 directly to the enter key 20.

Step S110: When the set key 6 is pressed, the input of patient ID is entered. After verification of the patient ID, the controller 9 then instructs the display switching component 10 to display a sensor ID input screen on the display component 2, and input of sensor ID (an example of input information or identification information about the sensor) is accepted. The input operation is the same as with the input of the operator ID.

Step S111 and S112: Once the input of the last character key for the sensor ID is complete, the home key 8 is pressed by the user. At this point the controller 9 instructs the display switching component 10 to move the cursor on the display component 2 directly to the enter key.

Step S113: Once all of the above-mentioned input of ID information is complete, the controller 9 then controls the display switching component 10 so as to display a blood deposit standby screen, as shown in FIG. 3B.

Step S114: When the measurement component 11 detects, via the sensor mounted to the sensor mounting component 12, that blood has been deposited, the controller 9 controls the display switching component 10 so as to display a measurement screen.

Step S115: When a measurement result is outputted by the measurement component 11, the controller 9 controls the display switching component 10 so as to display a measurement result on the screen.

Step S116: When the user presses the power switch 7, the controller 9 turns off the power (alternatively, this may be done with a timer, etc.).

1.3.2 Input Processing for Management Menu

Figure 8A:
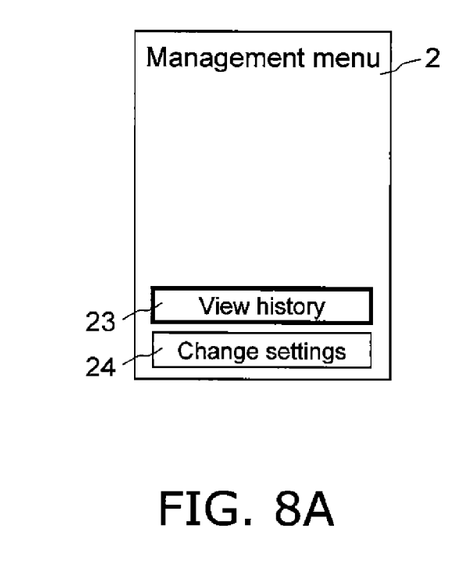
FIG. 8 shows an example of what is displayed on the display component of the biological sample measurement device.

Step S121: Meanwhile, when the management menu has been selected in step S103, the management menu shown in FIG. 8A is displayed on the display component 2. The management menu includes a history menu area 23 and a setting change menu area 24, and of these, the history menu area 23 is highlighted.

Figure 8B:
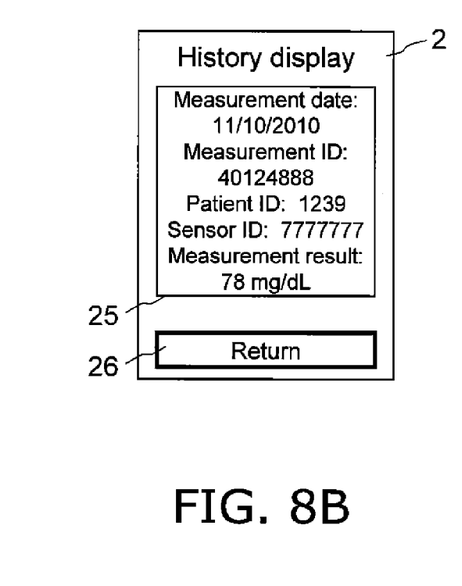

Step S122: If the user presses the set key 6 in a state in which the management menu is being displayed on the display component 2, the controller 9 instructs the display switching component 10 to display a history display 25 on the display component 2 as shown in FIG. 8B. A return menu area 26 is displayed beneath the history display 25.

Figure 8C:
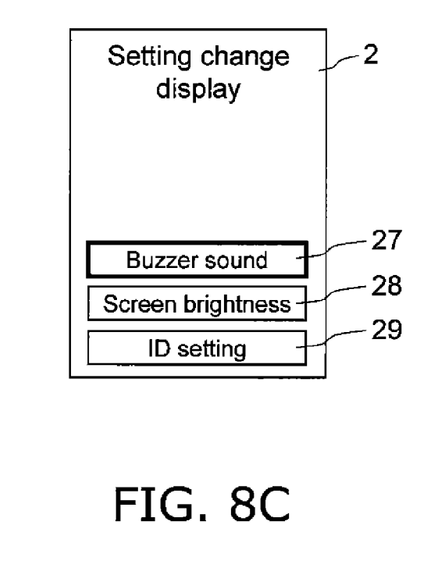

Step S123: Meanwhile, if the setting change menu area 24 is selected and the user presses the set key 6 in Step S121, display is performed for changing the settings, as shown in FIG. 8C. More specifically, the display of the setting changes includes a buzzer sound menu area 27, a screen brightness menu area 28, and an ID setting menu area 29.

In steps S121 to S123, if the home key 8 is pressed, the controller 9 controls the display switching component 10 so as to switch the screen of the display component 2 to the operator ID input screen (step S104).

1.3.3 ID Input Processing

The various ID inputs of steps S104 to S112 in FIG. 3A will now be described using the input of patient ID as an example.

Figure 4B:
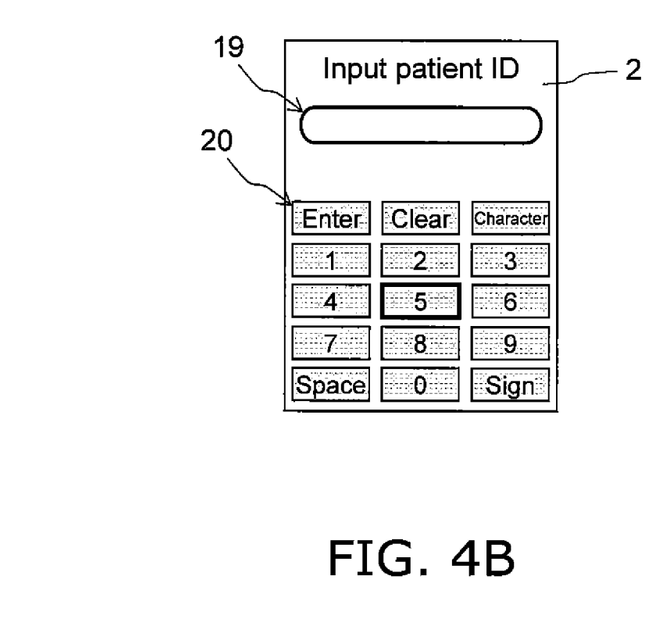
Figure 5:
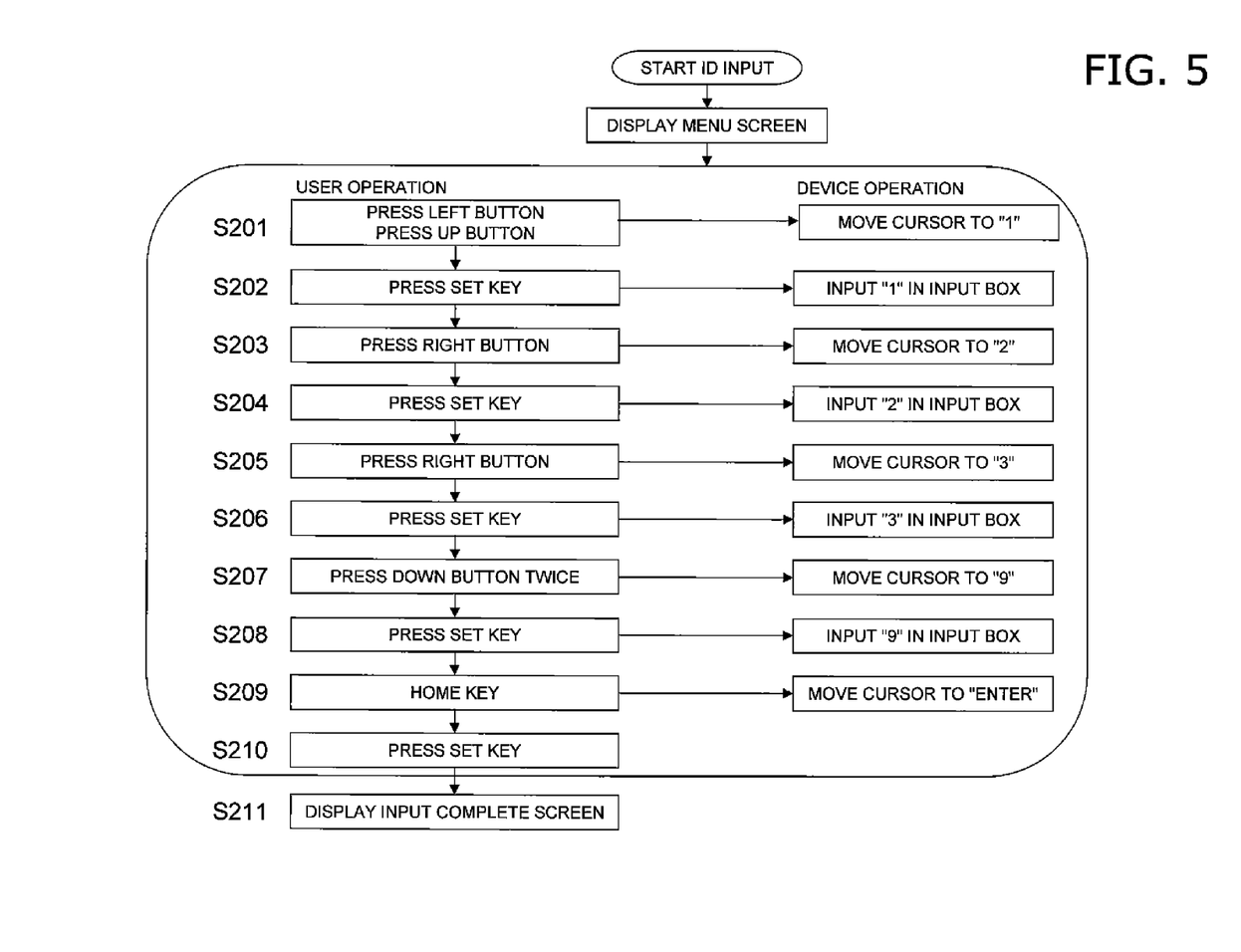
FIG. 5 is a diagram of the ID input operation with the biological sample measurement device.
Figure 6:
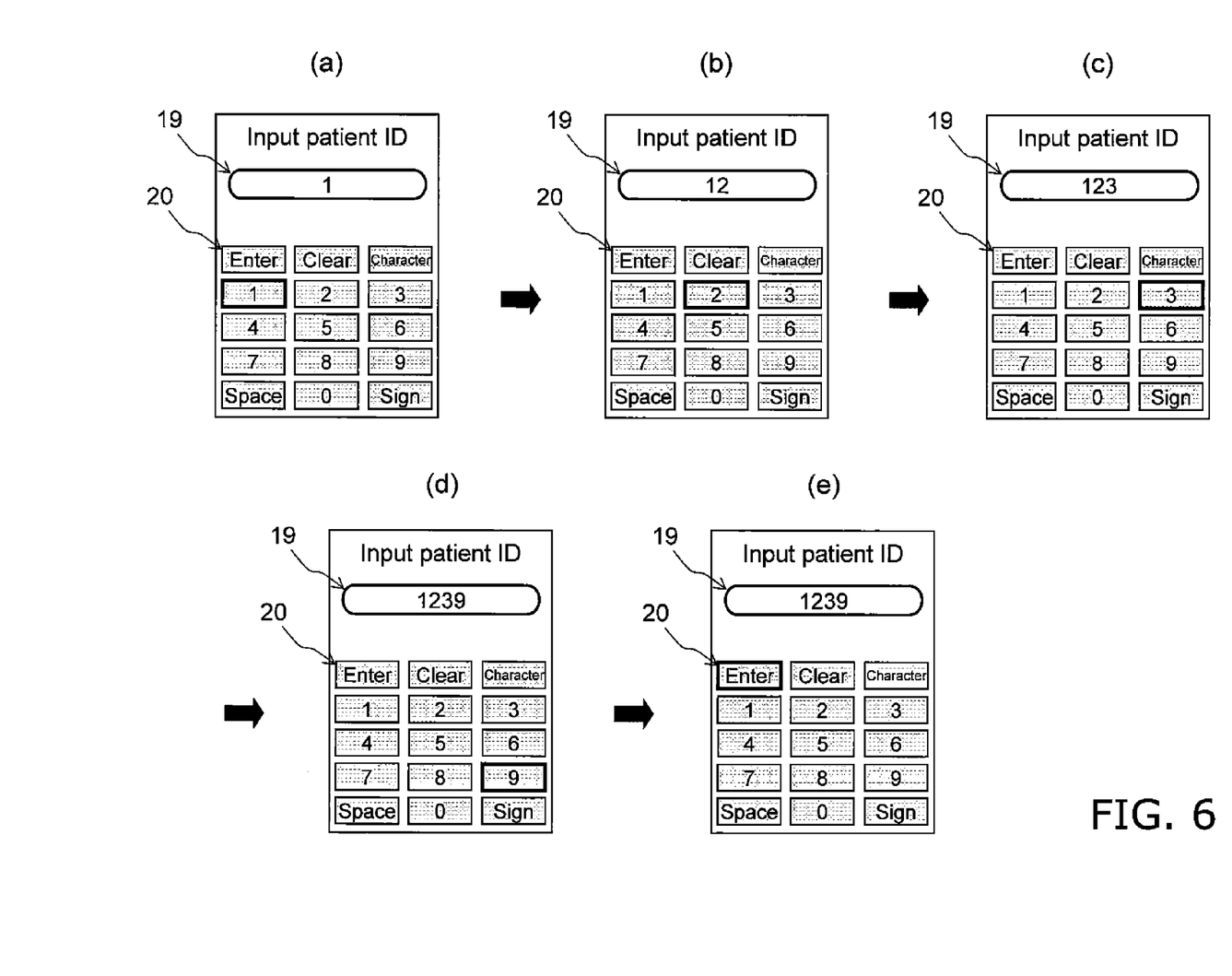
FIG. 6 shows an example of what is displayed on the display component of the biological sample measurement device.

FIG. 4B shows the display state of the display component 2 for inputting patient ID after the completion of operator ID input. As shown in this drawing, a character string display component 19 is displayed at the upper part of the display component 2, under which are displayed keys indicating the numerals 0 to 9 (other codes are not labeled to avoid making the description too complicated), the enter key 20 for entering the character string displayed on the character string display component 19, and so forth. FIG. 5 shows the input operation for a patient ID (such as 1239). FIG. 6*a* shows the state when the first digit "1" of the patient ID has been displayed.

In this embodiment, the term "character" encompasses numerals, symbols, signs, etc.

Step S201: With the display in FIG. 4B, the cursor is highlighting the "5" key. First, the user presses the cross key 5 to move the cursor to the "1" key on the display component 2 via the controller 9 and the display switching component 10.

Step S202: Next, when the set key 6 shown in FIG. 1 is pressed, "1" is displayed on the character string display component 19 as shown in FIG. 6*a*.

Step S203: Next, the user presses the cross key 5 to move the cursor to the "2" key on the display component 2 via the controller 9 and the display switching component 10.

Step S204: When the set key 6 shown in FIG. 1 is pressed, "12" is then displayed on the character string display component 19 as shown in FIG. 6*b*.

Step S205: The user then presses the cross key 5 to move the cursor to the "3" key on the display component 2 via the controller 9 and the display switching component 10.

Step S206: When the set key 6 shown in FIG. 1 is pressed, "123" is then displayed on the character string display component 19 as shown in FIG. 6*c*.

Step S207: The user then presses the cross key 5 to move the cursor to the "9" key on the display component 2 via the controller 9 and the display switching component 10.

Step S208: When the set key 6 shown in FIG. 1 is pressed, "1239" is then displayed on the character string display component 19 as shown in FIG. 6*d*.

Step S209: The above operation completes the input of patient ID "1239," so this patient ID (1239) is to be entered.

At this point, the conventional approach would be to use the cross key 5 to move the cursor, which was last located at the "9" key, successively to the "9," "8," "7," "4," and "1" keys and then the enter key 20, then press the set key 6 in this state to enter the patient ID (1239). However, thus moving the cursor, which had moved to the last key "9" to the enter key 20 took too long, making the device less convenient to use.

In view of this, in this embodiment, when the home key 8 in FIG. 1 is pressed while the input screens of steps S104, S107, and S110 in FIG. 3A are being displayed, the cursor is moved directly from the numeral "9" to the enter key 20 on the display component 2, as shown in FIG. 6*e*.

Step S210: Finally, the set key 6 is pressed to enter the patient ID.

Figure 7A:
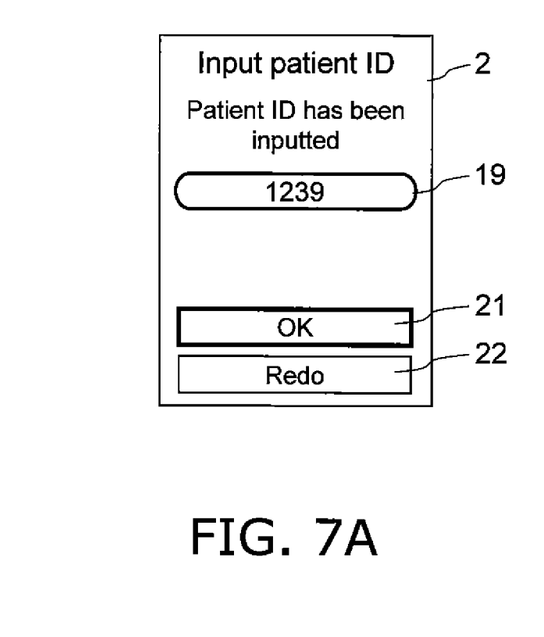
FIG. 7 shows an example of what is displayed on the display component of the biological sample measurement device.

Step S211: An input completed screen is displayed on the display component 2. At this point, the display component 2 displays the patient ID "1239" on the character string display component 19 as shown in FIG. 7A, beneath which are displayed a confirmation menu area 21 and a redo menu area 22. At this point the confirmation menu area 21 is highlighted. When the set key 6 is pressed, the controller 9 verifies the inputted patient ID.

Figure 7B:
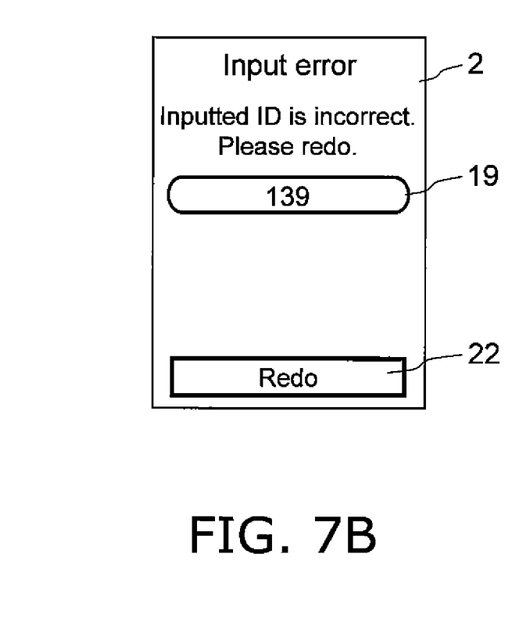

FIG. 7B shows the state when the set key 6 is pressed after unsuccessful input of the patient ID "1239." This is displayed when the controller 9 has determined that any one of the registered patient ID's does not match the inputted patient ID (that is, when verification of the identification information fails). At this point the redo menu area 22 is highlighted beneath the display component 2. When the set key 6 is pressed in this state, a patient ID input screen is displayed, and the input can be redone.

As discussed above, the operator ID, patient ID, and sensor ID are inputted in steps S104, S107, and S110 in FIG. 3A. The sensor ID is inputted by the barcode reader 13 shown in FIG. 2.

1.4 Features

With the blood glucose level measurement device 100 pertaining to this embodiment:

(i) the display component 2 displays, on the basis of commands from the controller 9, a plurality of character keys, the enter key 20 for entering input information including one or more characters inputted by selecting the plurality of character keys, and a cursor indicating which of the plurality of character keys is selected, (ii) the input component 3 has the cross key 5 that causes the controller 9 to successively move the cursor displayed on the display component 2 over the plurality of character keys so as to select one of the character keys, and the home key 8 that causes the controller 9 to change the display content of the display component 2, and (iii) when the home key 8 has been pressed in a state in which the input information is being displayed on the display component 2, the controller 9 moves the cursor displayed on the display component 2 from the selected character key directly to the enter key 20.

Therefore, in this embodiment, the efficiency of inputting identification information with a blood glucose level measurement device can be improved. Specifically, in a busy hospital or the like, when ID verification of each user is essential while there are numerous users of a single blood glucose level measurement device, there is a particularly great need to improve efficiency in this input operation. Also, because arrival at the enter key 20 is instantaneous after input of the last character, there is less likelihood of input errors due to mistaken operation of the cross key 5.

2. Other Embodiments

A blood glucose level measurement device is used as an example in the above embodiment, but some other biological sample measurement device may be used instead, and the present invention can also be applied to portable telephones, portable information terminal devices, and so forth. Furthermore, it can be applied not only to portable devices, but also to built-in information terminal devices.

INDUSTRIAL APPLICABILITY

The present invention is expected to find use as an information terminal device, such as a portable biological sample measurement device for measuring biological samples, such as blood glucose levels, in hospitals, for example.

REFERENCE SIGNS LIST 1 main body case
2 display component
3 input component
4 insertion opening
5 cross key
6 set key
7 power switch
8 home key
9 controller
10 display switching component
11 measurement component
12 sensor mounting component
13 barcode reader
14 time acquisition component
15 charging terminal
16 battery
17 measurement menu area
18 management menu area
19 character string display component
20 enter key
21 confirmation menu area
22 redo menu area
23 history menu area
24 setting change menu area
25 history display
26 return menu area
27 buzzer sound menu area
28 screen brightness menu area
29 ID setting menu area

What is claimed:

1. A biological sample measurement device for use by at least one user for measuring a biological sample of at least one patient, comprising:
a substantially cuboid main body case;
a display component provided on a surface on the first end side of the main body case;
an input component provided near the display component adjacent to a center of the main body case;
a controller connected to the input component and the display component, the controller being configured to control a display of the display component;
a sensor mounting component configured to mount a sensor thereon, the sensor being configured to have a biological sample deposited thereon, the sensor mounting component provided on a second end side opposite from the first end side of the main body case;
a data reader provided on a first end side of the main body case, the data reader being configured to read ID's of the at least one user, the at least one patient, and the sensor;
a finger groove provided on both sides of a part of the main body case on which the input component is provided; and
a measurement component connected to the controller, the measurement component being configured to detect and measure the biological sample, wherein:
the display component is configured to switch between a measurement screen and an input screen during a process during which input information is being displayed,
the display component is configured to display, based on commands from the controller:
a plurality of character keys,
an enter key for entering input information including one or more characters inputted by selecting one or more of the plurality of character keys, and
a selection marker indicating one of the plurality of character keys and the enter key being selected;
the input component includes:
a select key that causes the controller to successively move the selection marker displayed on the display component over the plurality of character keys so as to select one of the character keys,
a first key for changing a display content displayed on the display component, and
a set key for setting a character selected with the select key;
the select key is formed by a cross key;
the set key is formed by a first push button in a center of the cross key;
the first key is formed by a second push button provided near the cross key; and
the controller is further configured to:
accept input of the input information via the input component after a start of measurement processing by the measurement component,
display the character corresponding to a first character key in the display component when the set key has been operated in a state in which the first character key is being selected with the select key among the plurality of character keys, and
move the selection marker displayed on the display component from the selected character key directly to the enter key when the first key has been operated in a state in which the input information is being displayed on the display component.

2. The biological sample measurement device according to claim 1, wherein the first key is a change key for changing a display content of the display component.

3. The biological sample measurement device according to claim 1,
further comprising a display switching component configured to switch a display content displayed on the display component,
wherein the controller controls the display switching component so as to display a blood deposit standby screen.

4. The biological sample measurement device according to claim 1,
the selection marker displayed on the display component is moved from the enter key back to a selected character key indicating one of the plurality of character keys being selected by pressing the select key, the selected character key provided near the enter key.

* * * * *